United States Patent [19]

Wang

[11] 4,222,743
[45] Sep. 16, 1980

[54] METHOD AND APPARATUS FOR DETECTING BIOLOGICAL PARTICLES BY FLUORESCENT STAIN

[76] Inventor: Wei-Kung Wang, No. 13, Lane 100, Yen Chiu Yuan Rd., Sec. 2, Nan Kang District, Taipei, Taiwan

[21] Appl. No.: 926,342

[22] Filed: Jul. 20, 1978

Related U.S. Application Data

[63] Continuation-in-part of Ser. No. 764,613, Feb. 1, 1977, abandoned.

[51] Int. Cl.$^2$ .................... G01N 33/16; G01N 21/00
[52] U.S. Cl. .................... 23/230 B; 23/915; 250/365; 250/458; 250/461 B; 424/8; 424/12
[58] Field of Search .................... 23/230 B; 424/8, 12; 250/365, 458, 461 B

[56] References Cited

U.S. PATENT DOCUMENTS

| | | | |
|---|---|---|---|
| 3,876,504 | 4/1975 | Koffler | 23/230 B X |
| 3,904,367 | 9/1975 | Golibersuch | 23/230 B |
| 3,979,184 | 9/1976 | Gidever | 23/230 B X |
| 3,998,943 | 12/1976 | Ullman | 23/230 B X |
| 4,011,308 | 3/1977 | Gidever | 23/253 TP X |
| 4,020,151 | 4/1977 | Bolz | 424/12 X |
| 4,036,946 | 7/1977 | Kleinerman | 424/12 X |
| 4,056,724 | 11/1977 | Harte | 424/12 X |

Primary Examiner—Sidney Marantz
Attorney, Agent, or Firm—Ladas & Parry

[57] ABSTRACT

A metal-covered substrate is first adsorbed with a layer of known biological particles. This active substrate is then put into a solution containing an unknown amount of second biological particles that will bind the first kind of particles which are randomly distributed in the layer. A third biological particle bound to a fluorescent dye is applied to this substrate which is then placed in an apparatus having a light source inducing fluorescent emission, and a photon counting system to measure the amount of fluorescent photon. The metal-covered substrate reflects the exciting photon toward a photon trap so that few exciting photons will go to the photon counting system, while the induced signal is reflected toward the photon counting system and more induced signal will be measured.

36 Claims, 5 Drawing Figures

METHOD AND APPARATUS FOR DETECTING BIOLOGICAL PARTICLES BY FLUORESCENT STAIN

Continuation-in-part of Ser. No. 764,613, filed Feb. 1, 1977, abandoned.

BACKGROUND OF THE INVENTION

This invention relates to immunological and specific binding detection of biological particles; more particularly this invention relates to detection of biological particles such as antibody, hormone, specific binding protein, receptor and antigen by fluorescent and immunofluorescent dyes.

This invention relates to the subject matter of U.S. Pat. Nos. 4,011,308 "Method for Surface Immunological Detection of Biological Particles by the use of Tagged Antibodies," and 3,926,564 "Substrate for Immunological Tests and Method Fabrication Thereof," both granted to I. Giaever. Other publications related to the present invention are "Blood Coagulation Studies with the Recording Ellipsometer" by L. Vroman (National Bureau of Standards Miscellaneous Publication 256 September 1964); "A Study of Antigens and Antibodies by the Monolayer Film Technique of Langmuir" M. F. Shaffer and J. H. Dingle (Proceeding of Society of Experimental Biological Medicine 38, pages 528–530, 1938). "Immunological Reactions Between Film of Antigen and Antibody Molecule" by A. Rothen [Journal of Biological Chemistry Vol. 168 page 75–97 (April, May 1949)]; "The Beginnings of Immunofluorescence" by A. H. Coons (J. Immunology 87 pages 499–503 (1961)) "Fluorescent Protein Conjugates" by R. F. Steiner and H. Edelhock (Chemistry Review 62, pages 457–483 (1962), and "Radio-immunoassay" by D. S. Skeller et al. [Clinical Chemistry 19(2) pages 146–186 (1973)].

Immunological and specific binding reactions are highly specific biochemical reactions. The immunological reaction is vital in combatting diseases. The specific binding proteins and receptors are important in the transportation and balance of specific hormones, and molecules which affect the hormone function. To perform this kind of specific binding reaction on a metal surface, Shaffer et al., Rothen, and many other investigators have used ellipsometers to detect the amount of antibody bound to antigen or vice versa. Recently, Giaever has invented a visual detecting device using a specially prepared metal surface (see U.S. Pat. No. 3,926,564). Because the signal is detected by the naked eye, the quantitative determination is somewhat arbitrary.

According to this invention, a metal surface is used. No special preparation of the metal surface is needed. Most metals prepared by evaporation using a commercially available heating or sputtering device will meet the necessary requirement for this invention and produce a highly reflective metal surface. The metal is used to bind a monomolecular layer of protein, for example protein containing an antigen, while the amount of antibody (second biological particle) bound to this antigen is determined by the induced fluorescent emission from the fluorescent dye that is bound to an antibody (third biological particle) of this antibody.

The principal object of my invention is to provide an easy method and an apparatus to detect immunological or specific binding reactions. Another object of my invention is to provide an apparatus and an easy method to detect biological particles in a solution that may be serum, body secretion, body fluid, urine, tissue extraction etc. The biological particle may be a small particle like hormones, antibodies, plasma proteins, or a large particle like a virus, bacteria, cells, that are capable of stimulating antibody production. A further object of my invention is to provide an apparatus and simple method to perform diagnostic tests. In order to perform such a test, two appropriate biological particles with high mutual binding affinity must be found, one of them must be protein or protein bound (for example steroid hormone or polypeptide bound to bovine serum albumin) and the other a third biological particle, usually the antibody of the second biological particle. Because the novel apparatus according to the invention is used for quantitative signal detection, the metal surface need not be prepared from a particular kind of alloy or have a controlled thickness and the first biological particle, second biological particle and third biological need not form a layer so as to be detected. The preselected protein layer is absorbed on the surface of the substrate in a monomolecular layer (which includes first biological particle). When a suspect solution is tested for the presence or absence of the biological particle of interest (second biological particle), the monomolecular protein layer is placed in contact with the suspect solution for a sufficient long period of time to permit a specific binding reaction to occur. If the biological particle of interest is present, a specific reaction occurs between the initial protein layer and the biological particle of interest, resulting in some binding between them. This invention uses fluorescent or immunofluorescent stain to detect the amount of the second biological particle that is bound to the substrate. Immunofluorescent stain has long been used in histochemistry to detect the presence of antigen. In a traditional procedure, the antibody of the specific antigen is prepared and coupled with fluorescent dye. This fluorescent antibody is used as dye to stain a tissue slice, and a fluorescence microscope is used to visualize the existence of the specific antigen in the tissue. In this invention, we use the fluorescent antibody or specific binding protein to recognize the second biological particle that is bound to the first biological particle which is bound to the metal surface.

Figure 1:
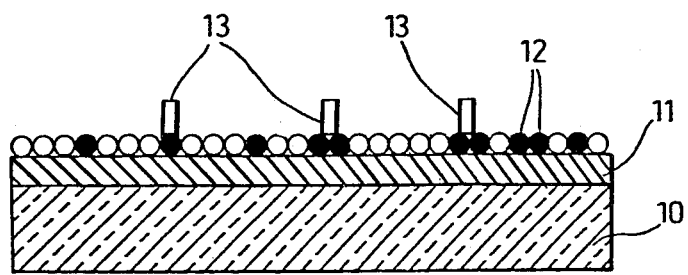
FIG. 1 is a sectional elevation view of the apparatus in accordance with this invention showing a substrate having second biological particles bound to the first biological particles within the monomolecular layer of protein.
Figure 2:
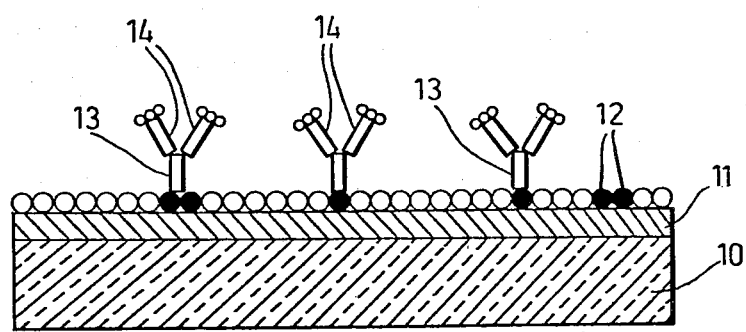
FIG. 2 in a sectional elevation view of the apparatus in FIG. 1 having the third biological particles bound to the second biological particles.
Figure 3:
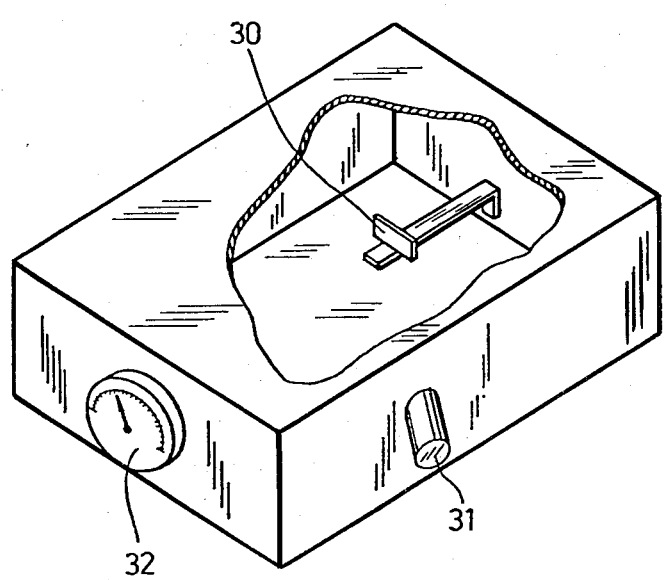
FIG. 3 is a view, partially cut away, of the apparatus in accordance with one embodiment of this invention for examining the finished substrate. The photon counting system in some distance away from the substrate to allow the exciting particles to be reflected by the metal surface toward the dark enclosure which will absorb all the photons that hit it, while even more induced signal from the substrate may travel toward the photon counting system due to reflection.

After some biological particles of interest (second biological particle) are bound to the first layer of protein, the substrate is as shown in FIG. 1 with substrate 10, metal surface 11, first biological particles 12, second biological particle 13. A biological particle, most probably the antibody of the second biological particle is conjugated with fluorescent dye. A drop of this fluorescent antibody (third biological particle) solution is applied to the substrate that has second biological particle as shown in FIG. 1. The substrate is then preferably stored in a moist chamber for a time interval sufficient so that the fluorescent antibody will react with the second biological particle. The substrate after this reaction is shown in FIG. 2. The amount of the bound fluorescent antibody 14 will be proportional to the amount of the second biological particle present on the substrate 30. The apparatus, arranged as shown in FIG. 3 is in a closed box with a light source 31 that is used to induce fluorescent emission from the substrate 30. The photon from 31 after hitting the substrate 30, which has a reflective metal surface, will be reflected toward the wall of the enclosure and trapped, while the induced signal will be detected by the photon counting system 32 that is used to measure the quantity of this fluorescent emission. Since a constant light source is used, the signal detected at photon counting system 32 is proportional to the amount of fluorescent antibody 14 at the substrate. Because of this newly invented apparatus, the biological particle of interest (second biological particle) need not form a layer in order to be detected. The second biological particles are bound to the first layer of protein. Since the second biological particle need not form a layer to be detected, the first biological particle need not occupy the whole layer. Therefore, the first layer of protein need not be a highly purified one. All these are definitely advantages compared to U.S. Pat. Nos. 3,926,564 and 4,011,308.

A further advantage is that the signal detection in this method is not related to the size of the biological particle.

This apparatus and method can detect both large biological particles (comparable to U.S. Pat. No. 3,853,467) and small biological particles (comparable to U.S. Pat. No. 3,926,564). It can also detect smaller particles like steroid hormone and polypeptide. The conjugated fluorescent dye may be derived from (A) Fluorescein Derivatives, the most commonly used of which are fluorescein isocyanate (FIC) and isothiocyanate (FITC), (B) Rhodamine derivatives, the most commonly used of which are rhodamine isocyanate and isothiocyanate, lissamine rhodamine B200 sulfonyl chloride (RB200XC), and (C) 1-Dimethyl-aminonaphthaline-5-sulfonyl chloride (DANSC); these dyes are commercially available (for example, Baltimore Biological Lab) and some fluorescent dye conjugated antibodies are also commercially available. For different dyes, a different light source and different photon detecting device should be used. The most intensified light source is laser. One may also use arc lamps with a light wavelength selecting device or tungsten lamps with a light wavelength selecting device to selected the favorable wavelength. The highly reflective surface of the invention reflects the exciting photons away from photo counting system 32 so avoiding a mixture of exciting photons and induced signal. The greater the mixture, the more noise there is. The higher the signal to noise ratio, the more reliable the test results are. No matter what light source is used, the photon detecting device also needs a wavelength selecting device to further selected the fluorescent emissions, which may be mixed with a small amount of exciting photon however because of the reflecting device, the signal to noise ratio is greatly increased. The wavelength selecting device may be a monochromator or filter.

The exciting signal disclosed in this invention need not be limited to photon. It may be neutron and the induced signal may be $\gamma$-ray (as is known neutron activation analysis) or other radiation, it may also be electrons or other charged particles and the induced signal may well by the characteristic X-ray if the third biological particle is labeled with some specific elements.

The amount of the induced signal to be measured can be manipulated by changing the quantity of the exciting signal. According to this invention, the exciting particle are directed away from the signal detecting system, so that the signal is greatly increased without significant increase of the noise. In the apparatus disclosed, a metal covered substrate without biological particles will give few noise counts. This is an improvement over the prior art using emanation of a signal from a source which has a constant value depending on the specific activity. Besides, emanation will decrease with time, sometimes at very short half life, and is therefore more difficult to work with. Having a induced signal is definitely an advantage of this invention over U.S. Pat. No. 4,011,308.

For induced signal, the natural background can be measured by turning off the exciting signal, therefore, there is no need to deposit the biological particle to form a special pattern as required by U.S. Pat. No. 4,011,308. The count outside the pattern is what is meant by the natural background.

Using the disclosed apparatus, it was possible to study a trace amount of the third biological particle on the metal surface since it was discovered that the third biological particle need not form a layer to be detected, and neither does the second biological particle or the first biological particle. Partially purified first biological particle (for example, after ammonium sulfate precipitation) was used as the first layer. The small amount of second biological particles will extend from the metal surface, and so will the third biological particles. This is an advantage compared to the use of layers because the particles of interest extending into the solution will facilitate the specific reaction and reduce the non-specific binding. Both the time for performing such a test and the amount of non-specific binding will be greatly reduced. Among the other advantages of this method compared to U.S. Pat. Nos. 4,011,308 and 3,926,564 in which the first, second or the third biological particles are forming layers so as to be detected (Giaever Slides) are: (1) Only a very small amount (about 1/1000 of that used by Giaever) of first biological and second biological particle is needed to perform a test. The first biological particles may be partially purified ones which are much easier to obtain and are therefore much cheaper. (2) Effect of equilibrium constant: If the first biological particles form a layer, a binding with the metal is needed to prevent these particles form dissolving and a large amount of first biological particle is required to achieve this. When second biological particles also form a layer, it is the binding between the first and the second biological particles that prevent the second biological particles from dissolving. However, during the formation of the second biological particle layer, there is a minimum concentration requirement of second biological particle in the solution. Below this minimum concentration, the second biological particle layer cannot be formed. This will greatly decrease the resolution of the test. In the disclosed method, there is no second biological particle layer. The amount of first biological particle in the protein layer may also vary dependent on degree of purification, or on addition of different amounts of inert protein such as BSA. The best resolution is much more sensitive and its limits depend on the amount of the third biological particle that can be measured accurately.

The apparatus shown in FIG. 3, which will be further discussed, is the key for the application of this disclosed method. The most important feature of the apparatus shown in FIG. 3 is that the metal substrate is used as part of the apparatus. There should be nothing in the path of the exciting photon which starts from light source 32 and ends at the wall of the dark enclosure except the highly reflective metal surface and the biological particles that are on it. With the incident angle being equalto the reflecting angle and the signal detecting system being perpendicular to and at some distance away from the substrate, the exciting particle will not be scattered toward the detecting system. The enclosure may also have a specially designed configuration to increase the trapping ability, so that almost all the exciting particle reflected toward the well-designed trap will stop there and will not be detected by the signal counting system. The induced signal that starts from the third biological particle after the absorption of the exciting particle may travel in any direction and some will go to the photon counting system depending on the collecting apperture of the photon counting system. Because of the highly reflective metal surface, those induced photons that travel directly away at opposite direction from the photon counting system may also be reflected backward and enter the photon counting system. The disclosed apparatus is designed especially for a highly reflective substrate and whether it is a metal covered one is not essential. A metal covered substrate is just one of the most convenient substates. For example, a thin layer of gel on the metal covered substrate will also be a good substrate. Whether the bound molecules are protein molecules or not is not essential either, this apparatus may also apply to other molecules or a thin tissue slice and many other things that are attached to such a highly reflective substrate by drying, chemical reaction, adhesion, binding or other means.

The disclosed apparatus also allows for a very high intensity light source to be used on a dry sample as in the present case. Because of the highly reflective metal surface, very little photon absorption (that will be converted to heat) will occur on the substrate, therefore there is little chance of fading or damaging the sample. For this reason, even laser may be used as the light source. All these are definitely advantageous compared to U.S. Pat. Nos. 4,056,724 and 4,036,946.

There will be different ways to bind the first biological particles to the substrate. For a metal covered substrate, a general immersing step may be used, and similarly for the binding of second biological particles to the first biological particle and the binding of the third biological to the second biological particle (the first biological particle in FIG. 5). To speed up the test, the sample may be dried on the substrate. To reduce the non-specific binding, the solution will be prevented from drying by keeping the substrate in a moisture chamber. There are many other modifications which may be used such as confining the sample in a small tube to limit the contact with the substrate in a small area, or using a breaker to enlarge the volume of the sample solution. No matter which way is used, washing the finished substrate is essential. Because the metal surface will bind the first biological particles, the first biological particles will bind the second biological particles and so on, the washing will remove the non-specific binding but not the specific reaction. However for glass, plastic and many other substrates, there is no binding between first biological particles and the substrate, and the wash then may randomly remove the specific reaction while no wash will keep the non-specific reaction on the substrate and therefore will make the quantitative measurement impossible.

Besides, such substrates are not highly reflective and will not be able to have good resolution in the disclosed apparatus.

To increase the quantitative resolution of the test and refine the reaction, a substrate of equal area and the same amount of sample solution should be used in one set of tests.

The absorption and emission spectra of most of the fluorescent compounds used in protein tracing were reported by Hansen P.A. (1964) [Publication from University of Maryland College Park, Md.]. The peak wavelength of the filter or monochromator to be used should follow this data. However, it was found that on using one piece of commercially available (Oriel Corporation) narrow band interference filter which has a transmission outside a pass band of 0.01%, this is not good enough to measure a trace amount of third biological particle on the substrate, because the noise of the instrument (to read a bare metal surface) is still high.

On using two pieces of such narrow band filter as a group for both the exciting signal filter and the induced signal filter, the resolution becomes very good and the noise of the instrument becomes non-detectable.

Both the absorption and emission band are vary broad according to Hansen, and become even broader when attached to a metal surface according to the invention. The exact peak wavelength for these narrow band interference filters is not important. However it was found that it is better to have two pieces of filter used as a group to have the same peak wavelength and similar band width.

When a laser is used as the light source the exciting signal filter need not be used. Monochromators are an excellent way to select the exciting signal, expecially when high intensity light sources are used.

It is easy to produce antibody to antibody of other species. For example, one may easily produce goat antibody to rabbit γ-globulin by injecting γ-globulin of rabbit into goat, and vice versa. The goat antibody to rabbit γ-globulin bind rabbit antibody and the rabbit antibody to goat γ-globulin will bind the goat antibody. Thterefore the fluorescent antibody need not bind directly to the second biological particle, it may come after the fourth biological particle, as shown in Example 2. The fluorescent antibody complement may also be used as the third biological particle, if the second biological particle is the antibody to the first biological particle. The amount of bound complement will be proportional to the amount of bound second biological particle.

EXAMPLE 1

The first layer protein contains HCG (human chorionic gonodotropin), the second biological particle is rabbit antibody to HCG. The third biological particle is fluorescent dye conjugated goat antibody to rabbit γ-globulin. The finished substrate is shown in FIG. 2: HCG-12, rabbit antibody to HCG 13, fluorescent dye conjugated goat antibody to rabbit γ-globulin 14.

EXAMPLE 2

Figure 4:
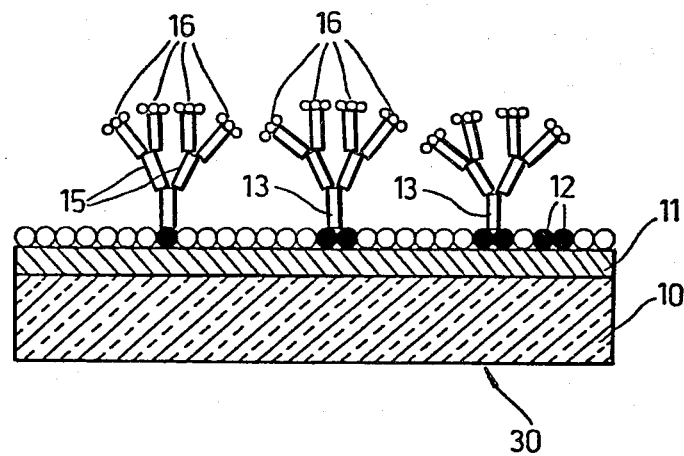
FIG. 4 is a sectonal elevation view of the apparatus in FIG. 1 having fourth biological particles bound to the second biological particles bound to the first biological particles.

The detection of HCG antibody may also be done by fluorescent dye conjugated rabbit antibody to goat γ-globulin. The first layer protein contains HCG, second biological particle is rabbit antibody of HCG. Before the third biological particle (fluorescent dye conjugated rabbit antibody to goat γ-globulin) is applied to the substrate, the fourth biological particle (goat antibody to rabbit γ-globulin) is applied. The finished substrate is shown in FIG. 4: HCG 12, rabbit antibody to HCG 13, goat antibody to rabbit γ-globulin 15, fluorescent dye conjugated rabbit antibody to goat γ-globulin 16.

EXAMPLE 3

Figure 5:
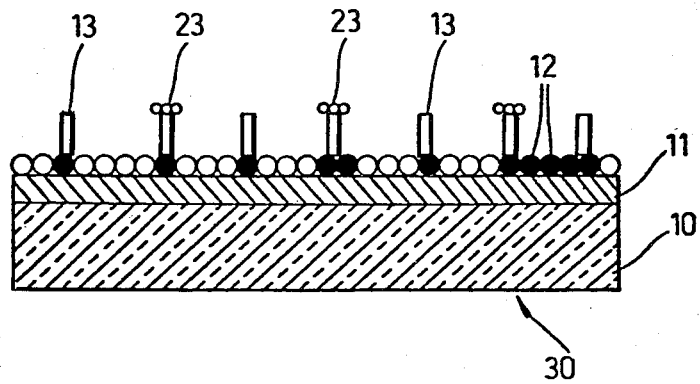
FIG. 5 is a sectional elevation view of the apparatus in FIG. 1 having the third biological particles bound to the first biological particles.

Another way to detect HCG antibody is to use fluorescent dye conjugated rabbit antibody to HCG as the third biological particle. The finished substrate is shown in FIG. 5 with HCG 12, rabbit antibody to HCG 13, fluorescent dye conjugated rabbit antibody to HCG 23. An increased amount of 13 will reduce the amount of 23.

EXAMPLE 4

To detect the HCG, we may use HCG as the first biological particle, rabbit antibody to HCG as the second biological particle, fluorescent dye conjugated goat antibody to rabbit γ-globulin as the third biological particle. When we immerse the substrate with first layer of protein into the fluid of interest to determine the amount of HCG in it, we may add known amount of rabbit antibody to the fluid, this added antibody may bind either the HCG on the substrate of HCG in solution. The amount of HCG on the substrate is a constant, the more HCG is in the solution, the less the amount of antibody which binds to the substrate. The finished substrate is the same as Example 1. A similar method may also be applied to Example 2, or Example 3 to detect the amount of HCG in a fluid.

EXAMPLE 5

To detect HCG, we may use rabbit antibody to HCG as the first biological particle, HCG as the second biological particle, and fluorescent dye conjugated rabbit antibody to HCG as the third biological particle. The finished substrate is shown in FIG. 2 with rabbit antibody to HCG 12, HCG 13, fluorescent dye conjugated rabbit antibody to HCG 14. This method is especially useful to detect large biological particle like virus, bacteria and cells. (All the biological particles used in these examples are from Baltimore Biological Laboratory).

I claim:

1. Apparatus for detecting biological particles of a particular species in a fluid comprising
a substrate having
a metal film surface on which has been deposited an immunologic coating of at least one layer which comprises,
a layer of protein or protein bound particle adsorbed on said metal film surface with first biological particles randomly distributed therein,
means for applying some third biological particles to the substrate after the substrate has been exposed to a fluid containing suspected second biological particles;
means for producing exciting particles and means to direct said exciting particles toward said third biological particles; means for measuring the quantity of induced signal from said third biological particle and means to direct the exciting particle which have effected excitation away from the quantity measuring means.

2. The apparatus of claim 1 wherein:
said third biological particle comprises a fluorescent dye bound to a biological particle, said exciting particles are photons, said means to direct said exciting particle comprises means for directing photons,
said means for measuring the quantity of said induced signal comprises means to measure the quantity of fluorescent emission, said means to direct said exciting photons away from the quantity measuring means comprises said metal surface and a photon trap.

3. The apparatus of claim 2 including additional means for directing photons onto the metal film surface of said substrate.

4. The apparatus of claim 3, wherein said means for directing photons onto the metal film surface of said substrate comprises an enclosure having first and second end members wherein: a photon source within said enclosure adjacent to said first end member, said second member comprises means attached to a surface of said substrate to let the photons to be directed on it, said enclosure also comprises said photon trap.

5. The apparatus of claim 4 further including means in the enclosure for receiving the fluorescent emission.

6. The apparatus of claim 4, wherein said photon source comprises a laser.

7. The apparatus of claim 2, wherein said photon source comprises a lamp and a wavelength selecting device.

8. The apparatus of claim 5, wherein said means comprise a photon counting system and a wavelength selecting device.

9. The appparatus of claim 7, wherein said wavelength selecting device comprises a monochromator.

10. The apparatus of claim 7, wherein said wavelength selecting device comprises a filter.

11. The apparatus of claim 2, wherein said fluorescent dye comprises a fluorescein derivative.

12. The apparatus of claim 11, wherein said fluorescein derivative is fluorescein isothiocyanate.

13. The apparatus of claim 2, wherein said fluorescein dye comprises a rhodamine derivative.

14. The apparatus of claim 13, wherein said rhodamine derivative is tetra methyl rhodamine isothiocyanate.

15. The apparatus of claim 13, wherein said rhodamine dye derivative is lissamine rhodamine B 200 sulfonyl chloride.

16. The apparatus of claim 2, wheren said fluorescent dye is 1-dimethylaminonaphthalene-5-sulfonyl chloride.

17. Method for detecting biological particles of a particular species in a fluid which comprises the steps of:

immersing a substrate having a metal surface into a solution of first biological particle, salt and other kinds of protein for sufficient time to adsorb a monomolecular layer of protein, removing unbound protein by washing said substrate with water, immersing said substrate having said monomolecular layer of said protein thereon into said fluid whereby some of a second biological particle, if present in said fluid, is bound to said first biological particle;

means to apply third biological particle over the said substrate having said first biological particle and said second biological particle;

removing unbound particles by washing said substrate with water, examining said substrate by directing exciting particles toward said substrate, directing the exciting particles away from the quantity measuring means and directing the resulting induced particles toward said quantity measuring means to determine the quantity of the induced signal from the said substrate.

18. The method of claim 17, wherein said means to apply third biological particle comprises the step of immersing said substrate having said first biological particle and said second biological particle if present into a solution of the third biological particle to let the third biological particle bind to said substrate, and removing unbound particles by washing said substrate with water.

19. The method of claim 17, wherein said means to apply third biological particle comprises the steps of immersing said substrate having said first biological particle and said second biological particle if present into a solution of fourth biological particle to let it bind to said second biological particle, immersing said substrate having said first biological particle, said second biological particle and said fourth biological particle into a solution of third biological particle to let said third biological particle bind to said fourth biological particle, removing unbound particles by washing said substrate with water.

20. The method of claim 18, wherein:
said second biological particle is antibody to said first biological particle,
said third biological particle is fluorescent dye conjugated antibody to said second biological particle.

21. The method of claim 18, wherein:
said first biological is antibody to said second biological particle,
said third biological particle is fluorescent dye conjugated antibody to said second biological particle.

22. The method of claim 18, wherein:
said second biological particle is antibody to said first biological particle,
said third biological particle is fluorescent dye conjugated antibody to the complement of the complex of said first and second biological particle.

23. The method of claim 21, wherein:
said fourth biological particle comprises antibody to said second biological particle,
said third biological particle is antibody to said fourth biological particle.

24. The method of claim 18, wherein:
said second biological particle is a specific binding molecular to said second biological particle,
said third biological particle is fluorescent dye conjugated antibody to said second biological particle.

25. The method of claim 18, wherein:
one of said first biological particle and said second biological particle is the antibody of the other particle,
said third biological particle is the fluoresecent dye conjugated second biological particle.

26. The method of claim 18, wherein:
one of said first biological particle and said second biological particle is the specific binding molecular of the other particle,
said third biological particle is the fluorescent dye conjugated second biological particle.

27. The method of claim 18, wherein examining step more particularly comprises;
turning on the light source, directing the light from the light source to the area on said substrate where said third biological particle has been bound.

28. The method of claim 18, wherein said examining step more particularly comprises directing said exciting particles toward said substrate, arranging the substrate to direct the exciting light toward the photon trap, receiving and integrating induced signal from said substrate and indicating the integral quantity of said induced signal to provide a measure of the concentration of said biological particle in said fluid.

29. The apparatus of claim 8, wherein said wavelength selecting device comprises a monochromator.

30. The apparatus of claim 8, wherein said wavelength selecting device comprises a filter.

31. The method of claim 17, wherein said exciting particle are photons and said induced signal comprises fluorescent emission.

32. The apparatus of claim 4, wherein said first member and said second member are so arranged that said exciting photons that enter the enclosure will hit said metal surface and are reflected toward said photon trap.

33. A fluorometric testing apparatus comprising a highly reflective substrate having a surface portion for receiving a sample,
means to produce exciting photons and means to direct said exciting photons toward said sample, means for measuring the quantity of the induced photon from said sample, and means to direct the exciting photons which have effected excitation away from the quantity measuring means.

34. The apparatus of claim 33 wherein
said highly reflective substrate comprises metal covered substrate, said means to produce exciting photons comprises a wavelength selecting device and a light source,
said means to direct exciting photons away from the quantity measuring means comprises said metal covered substrate and a photon trap, said means for measuring the quantity of induced photon comprises a wavelength selecting device and a photon counting system.

35. The apparatus of claim 34 wherein
said exciting photon after hitting said substrate will be reflected toward said photon trap.

36. The apparatus of claim 35 wherein:
said wavelength selecting device of said means to measure the induced photon comprises two pieces of narrow band interference filters with similar peak wavelength.

* * * * *